United States Patent
Baarman et al.

(10) Patent No.: US 12,222,528 B2
(45) Date of Patent: Feb. 11, 2025

(54) SURFACE ILLUMINATOR HAVING A LINE EMITTER AND CONFIGURED TO DISINFECT A SURFACE

(71) Applicants: CORNING INCORPORATED, Corning, NY (US); UV PARTNERS, INC., Grand Haven, MI (US)

(72) Inventors: David W Baarman, Fennville, MI (US); Boyd Vern Hunter, Elmira, NY (US); Ming-Jun Li, Horseheads, NY (US); Xiao Li, Elmira, NY (US); Stephan Lvovich Logunov, Corning, NY (US)

(73) Assignees: CORNING INCORPORATED, Corning, NY (US); UV PARTNERS, INC., Grand Haven, MI (US)

( * ) Notice: Subject to any disclaimer, the term of this patent is extended or adjusted under 35 U.S.C. 154(b) by 450 days.

(21) Appl. No.: 17/688,142

(22) Filed: Mar. 7, 2022

(65) Prior Publication Data

US 2022/0282853 A1 Sep. 8, 2022

Related U.S. Application Data

(60) Provisional application No. 63/157,286, filed on Mar. 5, 2021.

(51) Int. Cl.
*G02B 5/02* (2006.01)
*A61L 2/00* (2006.01)

(52) U.S. Cl.
CPC .......... *G02B 5/0242* (2013.01); *A61L 2/0047* (2013.01); *G02B 5/0278* (2013.01)

(58) Field of Classification Search
CPC ....... G02B 5/0242; G02B 5/0278; A61L 2/10; A61L 2/0047
See application file for complete search history.

(56) References Cited

U.S. PATENT DOCUMENTS

| 7,450,806 | B2 | 11/2008 | Bookbinder et al. |
| 8,926,143 | B2 | 1/2015 | Li et al. |
| 11,083,810 | B2 | 8/2021 | Umenei et al. |
| 2008/0067417 | A1 | 3/2008 | Lane et al. |
| 2015/0144802 | A1* | 5/2015 | Bauco ........................ A61L 2/10 250/435 |
| 2017/0184772 | A1* | 6/2017 | Dykaar ................ G02B 5/0242 |
| 2017/0290934 | A1* | 10/2017 | Dobrinsky .......... G02B 19/0095 |
| 2022/0050252 | A1* | 2/2022 | Logunov .................... F21K 9/69 |

FOREIGN PATENT DOCUMENTS

| CN | 107073145 B | * 12/2020 | ............... A61L 2/10 |
| EP | 3043244 B1 | 9/2019 | |
| WO | WO-2020197064 A1 | * 10/2020 | ............... A61L 2/10 |

* cited by examiner

*Primary Examiner* — David E Smith
(74) *Attorney, Agent, or Firm* — Svetlana Z. Short (57) ABSTRACT

Disclosed herein are embodiments of an illuminator for disinfecting a surface. The surface defines a first plane. The illuminator includes a line emitter configured to emit light in a continuous line along at least a portion of at least one edge of the surface. The light has a peak wavelength in a range of 100 nm to 400 nm. The illuminator also includes a curved reflector surface and an exit aperture defining a second plane transverse to the first plane. The line emitter is positioned between the curved reflector surface and the exit aperture, and the curved reflector surface is configured to redirect the light from the line emitter through the exit aperture across the surface.

34 Claims, 11 Drawing Sheets

SURFACE ILLUMINATOR HAVING A LINE EMITTER AND CONFIGURED TO DISINFECT A SURFACE

CROSS REFERENCE TO RELATED APPLICATIONS

This application claims the benefit of priority under 35 U.S.C. § 119 of U.S. Provisional Application No. 63/157,286, filed on Mar. 5, 2021, the content of which is relied upon and incorporated herein by reference in its entirety.

BACKGROUND

The present invention generally relates to a surface illuminator and more particularly to a surface illuminator configured to disinfect a surface.

Ultraviolet light is known to inactivate certain pathogens. Such ultraviolet light can be produced by a variety of different light sources. However, not all sources are economical or efficient at providing uniform coverage of ultraviolet light over surfaces while maintaining a small form factor. For example, light emitting diodes are a common source of ultraviolet light, but several light emitting diodes are necessary to cover a large surface. When the light emitting diodes are arranged in an array to provide the desired coverage, gaps of coverage between emission cones of the light emitting diodes will inevitably develop. In order to provide adequate disinfecting coverage in these gap areas, the total irradiance of the system has to be increased, producing an inefficient and uneconomical excess light.

SUMMARY

One embodiment of the disclosure relates to an illuminator for disinfecting a surface. The surface defines a first plane. The illuminator includes a line emitter configured to emit light in a continuous line along at least a portion of at least one edge of the surface. The light has a peak wavelength in a range of 100 nm to 400 nm.

According one embodiment, the a line emitter is configured to emit light in a continuous line, the line emitter comprises a light diffusing rod structured to scatter light along its length, the light diffusing rod comprising at least one of: (i) a scattering layer, (ii) scattering particles, or (iii) voids; and a reflector surface optically coupled to the line emitter;

wherein the light diffusing rod is optically coupled to at least one light source and has a maximum cross-sectional dimension D between 0.5 mm to 20 mm; and the reflector surface is configured to redirect the light from the line emitter towards the surface.

One embodiment of the disclosure relates to an illuminator for disinfecting a surface. The surface defines a first plane. The illuminator includes a line emitter configured to emit light in a continuous line along at least a portion of at least one edge of the surface. The light has a peak wavelength in a range of 100 nm to 400 nm. The illuminator also includes a curved reflector surface and an exit aperture defining a second plane transverse to the first plane. The line emitter is positioned between the curved reflector surface and the exit aperture, and the curved reflector surface is configured to redirect the light from the line emitter through the exit aperture across the surface.

Another embodiment of the disclosure relates to a surface illuminator configured to disinfect a surface. The surface has a first surface area. The surface illuminator includes a line emitter configured to emit light in a continuous line along at least a portion of at least one edge of the surface. The light has a peak wavelength in a range of 100 nm to 400 nm. The surface illuminator also includes a curved reflector surface and an exit aperture arranged transverse to a first plane defined by the surface. The curved reflector surface is configured to redirect the light from the line emitter through the exit aperture over at least 90% of the first surface area.

Another embodiment of the disclosure relates to a method for decontaminating a surface having a first surface area. In the method, light having a peak wavelength in a range of 100 nm to 400 nm is emitted from a line emitter. The line emitter is configured to emit the light in a continuous line along at least a portion of at least one edge of the surface. Further, in the method, the light is reflected from a curved reflector surface through an exit aperture and onto the surface. The light irradiates at least 90% of the first surface area at a power density sufficient to disinfect the first surface area.

Another embodiment relates to a method for decontaminating a surface having a first surface area, the method comprising:

emitting light having a wavelength of 100 nm to 400 nm from a line emitter, the line emitter comprising a light diffusing rod and is configured scatter the light and to emit the scattered light in a continuous line along at least a portion of the surface, wherein the light diffusing rod comprises a material comprising least one of: (i) a scattering layer; (ii) scattering particles; (iii) voids; and reflecting the light from a curved reflector surface through an exit aperture and onto the surface, wherein the light irradiates at least 90% of the first surface area at a power density sufficient to disinfect the first surface area.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims.

BRIEF DESCRIPTION OF THE DRAWINGS

The accompanying drawings are included to provide a further understanding, and are incorporated in and constitute a part of this specification. The drawings illustrate one or more embodiment(s), and together with the description serve to explain principles and operation of the various embodiments. In the drawings.

DETAILED DESCRIPTION

Referring generally to the figures, embodiments of a surface illuminator are provided. The surface illuminator is configured to disinfect a surface, such as a touch panel, using ultraviolet light, especially ultraviolet light in the UV-C band. Embodiments of the surface illuminator include a line emitter, a curved surface reflector, and an exit aperture. Ultraviolet light from the line emitter is collected by the curved surface reflector and is directed out the exit aperture over the illuminated surface. In certain embodiments, the line emitter is a light diffusing rod configured to scatter ultraviolet light from a light source. Advantageously, the design of the surface illuminator has fewer components and provides more efficient disinfecting coverage than certain conventional designs. These and other aspects and advantages will be discussed in relation to the embodiments provided below and in the drawings. These embodiments are presented by way of illustration and not by way of limitation.

Figure 1:
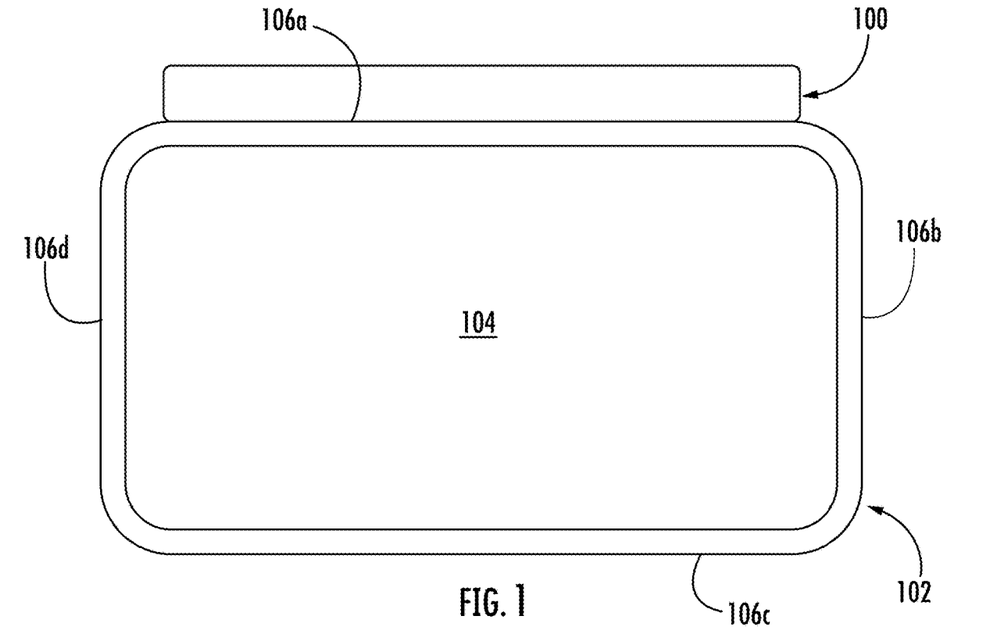
FIG. 1 depicts a surface illuminator used with a touch panel, according to exemplary embodiments.

FIG. 1 depicts an embodiment of a surface illuminator 100. The surface illuminator 100 is configured to disinfect any of a variety of surfaces using ultraviolet light (in particular light having a peak wavelength in the range of 100 nm to 400 nm), particularly ultraviolet light in the C band (UV-C), which has a peak wavelength in the range of 100 nm to 280 nm. In the embodiment depicted in FIG. 1, the surface illuminator 100 is positioned to disinfect a touch panel 102. In particular, the touch panel 102 includes a touch-enabled display surface 104. The touch panel 102 includes a plurality of edges, shown as edges 106a-106d, that bound the display surface 104. The surface illuminator 100 is positioned adjacent at least one edge 106a-106d in order to emit ultraviolet light onto the display surface 104 to disinfect it.

Figure 2:
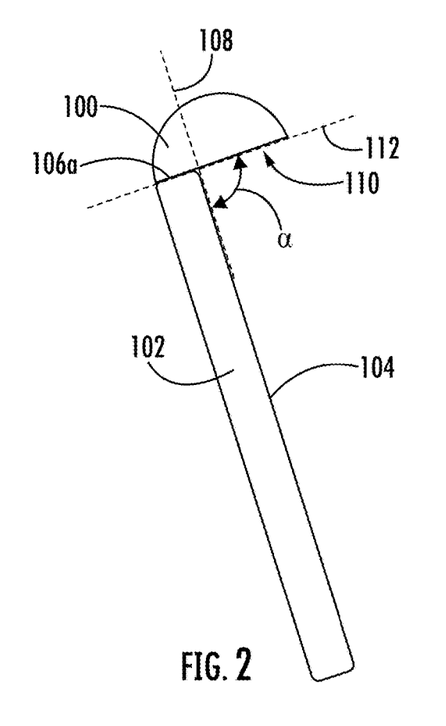
FIG. 2 depicts a side view of the surface illuminator and touch panel of FIG. 1, according to an exemplary embodiment.

FIG. 2 depicts a side view of the surface illuminator 100 and touch panel 102. The display surface 104 of the touch panel 102 defines a first plane 108. The surface illuminator 100 includes an exit aperture 110 that defines a second plane 112. The second plane 112 is transverse to the first plane 108. In embodiments, the second plane 112 forms an angle α with the first plane 108 of 70° to 90°, in particular 80° to 89°.

Figure 3:
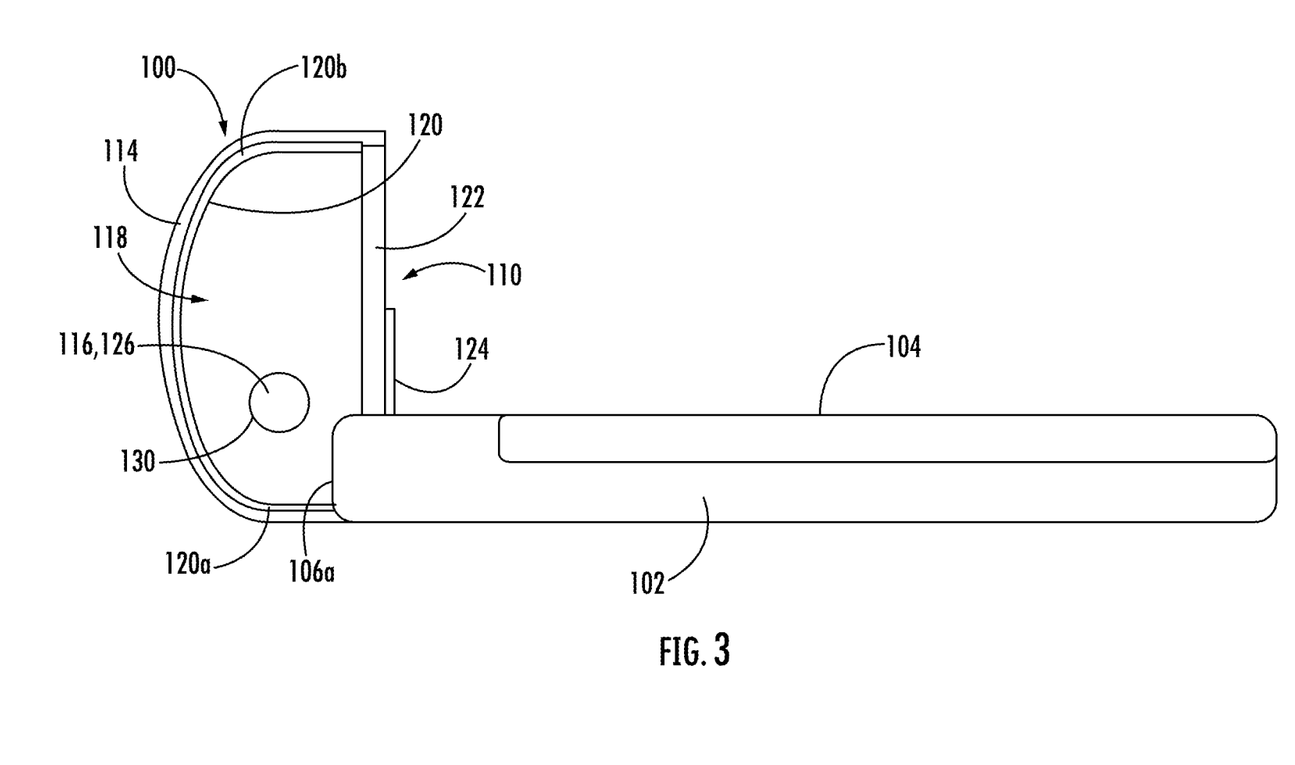
FIG. 3 depicts a detail and partial cross-sectional view of the surface illuminator and touch panel of FIGS. 1 and 2, according to an exemplary embodiment.

FIG. 3 depicts a cross-sectional view of the surface illuminator 100 as positioned on the edge 106a of the touch panel 102. In embodiments, the surface illuminator 100 includes a housing 114 configured to hold a line emitter 116. As used herein, a "line emitter" is an element configured to emit light continuously and uniformly over a length. In an embodiment, the line emitter 116 is a light diffusing rod. In another embodiment, the line emitter 116 is an ultraviolet-emitting discharge tube. In still another embodiment, the line emitter 116 is at least one light emitting diode extending continuously along the emitter length. Power for the surface illuminator 100 may be supplied by an internal power source (such as a battery) of the surface illuminator, a power source in the touch panel, or from an external source (e.g., a plug connected to an electrical outlet).

The housing 114 defines an interior 118 within which the line emitter 116 is positioned. In various embodiments, the housing 114 may be an integral part of an exterior shell enclosing all of the components of the surface illuminator 100, or the housing 114 of the surface illuminator 100 may be enclosed within said outer shell. Housing 114 includes a curved reflector surface 120. In the housing 114, the line emitter 116 is positioned between the curved reflector surface 120 and the exit aperture 110. Light from the line emitter 116 is collected by the curved reflector surface 120 and directed through the exit aperture 110 onto the display surface 104 of the touch panel 102. In embodiments, the light provided through the exit aperture 110 is at a power density sufficient to disinfect the all or a substantial portion of the display surface 104. For example, in embodiments, the light provided through the exit aperture 110 irradiates at least 90% of the surface area of the display surface 104, or at least 95% of the surface area of the display surface 104.

In embodiments, the curved reflector surface 120 comprises a substrate, preferably with an optical quality finish, with a highly reflective coating. For the UV-C band, a versatile coating comprises protected metal, such as aluminum with an overcoat. The substrate can be manufactured from a variety of materials, such as glass, metal, or plastic. In embodiments, the curved reflector surface 120 defines an extruded acylindrical shape such that the curved reflector surface 120 has the same cross-sectional profile along its length. An acylindrical surface can be defined as a function of height according to the relationship $$z = \frac{\frac{y^2}{R}}{1 + \sqrt{1 - (K+1)\frac{y^2}{R^2}}} + \sum_n C_n y^n$$

where R is the radius of curvature, K is the conic constant, $C_n$ is the aspheric coefficient for the n-th term in the series, y is the height above the optical axis and z is the position along the optical axis. The number of terms used in the power series is determined by the designer and may be as few as zero. Other asymmetric surface forms may also be used. Examples of such surfaces include toroids, anamorphic aspheres, and XY polynomials, among others. Further, in embodiments, the radius of curvature and.or aspheric coefficient can be varied (continuously or discontinuously) as a function of the x-coordinate for certain applications.

Ultraviolet light from the line emitter 116 illuminates the curved reflector surface 120, and the curved reflector surface 120 directs the ultraviolet light through the exit aperture 110. As shown in FIG. 3, the exit aperture 110 includes a window 122. The window 122 is made of a material that is transparent to ultraviolet light, such as high purity fused silica, specialized glasses, or certain plastics. In embodiments, the material of the window 122 transmits at least 50%, at least 60%, at least 70%, at least 80%, or at least 90% of light in the range of 100 nm to 400 nm through the thickness of the window 122. In one or more embodiments, the material of the window 122 transmits at least 90% of light at least a portion of the range of 100 nm to 400 nm (e.g., 100 nm to 350 nm, 100 nm to 300 nm, 100 nm to 250 nm, 100 nm to 200 nm, 150 nm to 400 nm, 200 nm to 400 nm, 250 nm to 400 nm, 300 nm to 400 nm, or 200 nm to 300 nm) through the thickness of the window 122.

In embodiments, the window 122 includes a coating 124 configured to reduce transmission of the ultraviolet light over a portion of the window 122. For example, in embodiments, the coating 124 covers 50% of the window 122 or less, in particular 40% of the window 122 or less, more particularly about 33% or less. Further, in embodiments, the coating 124 covers at least 20% of the window 122. The coating 124 is neutral density filter having an optical density of at least 1.0, or at least 1.5, or at least 2.0. In embodiments, the neutral density filter has an optical density of at most 3.0. Further, in embodiments, the coating 124 may have a gradient of neutral density filter in which a higher optical density is provided at the bottom of the window 122 with a decreasing optical density as the neutral density filter extends toward the top of the window 122.

Figure 12:
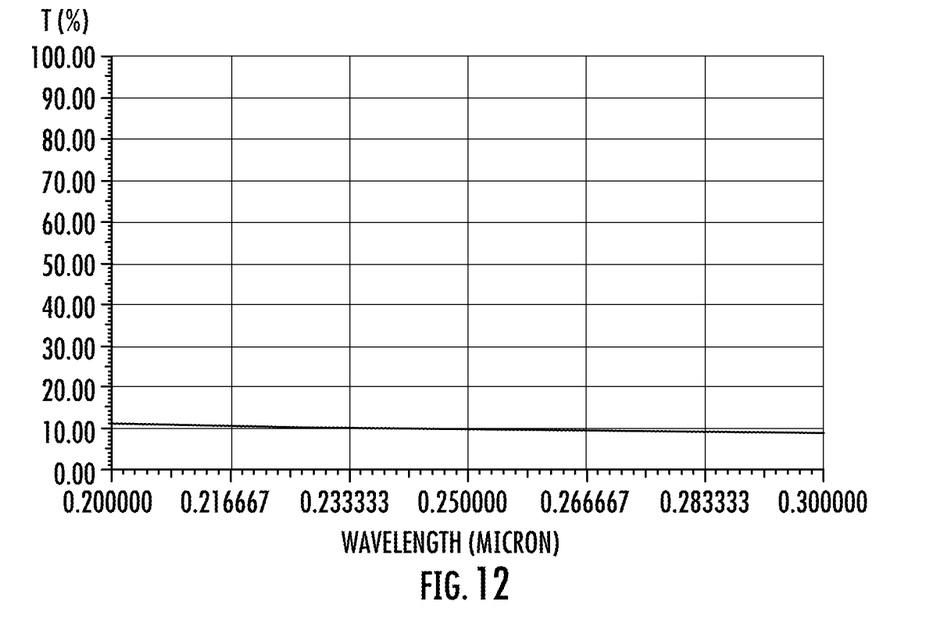
FIGS. 12-14 depict plots of transmittance and reflectance for a neutral density filter coating of the exit aperture window according to an exemplary embodiment.
Figure 13:
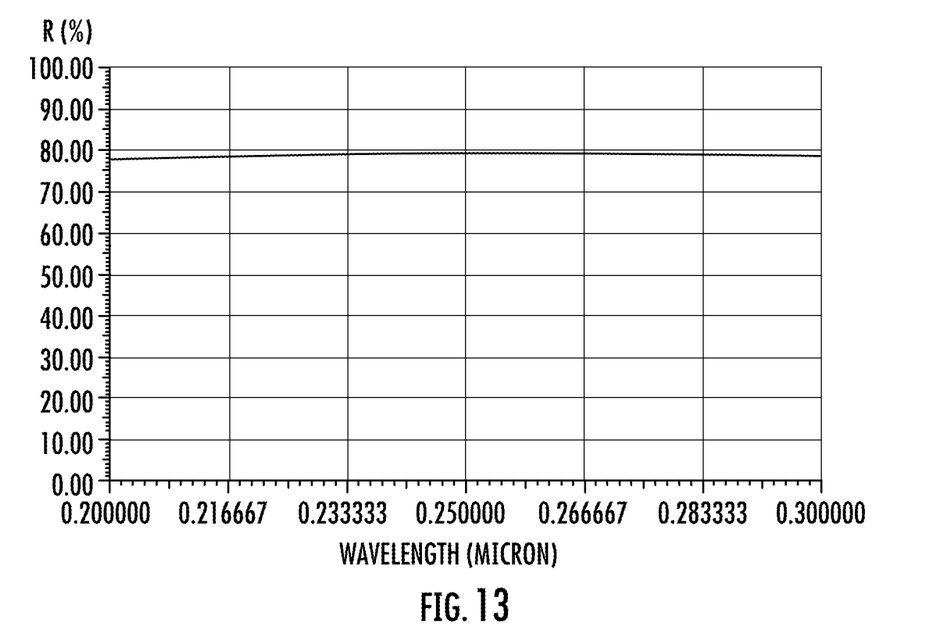

An exemplary embodiment of a coating 124 that operates as a neutral density filter is a coating of aluminum with magnesium fluoride. In general, metal layers work well as neutral density filters because metals are less sensitive to wavelength and incident angle. However, a neutral density filter made of a dielectric coating stack could also be used. At a wavelength of 265 nm, aluminum has an index of refraction with a real part of 0.216 and an imaginary part of 2.163, and magnesium fluoride has an index of refraction with a real part of 1.299 and an imaginary part of 0.000. In order to prepare a coating 124 that acts as a neutral density filter with an optical density of 1.0, the coating is provided with an optical thickness of 0.530 (0.241 Al and 0.289 $MgF_2$) and a thickness of 0.0748 μm (0.0202 μm Al and 0.0546 μm $MgF_2$). The optical density can be increased from 1.0 by increasing the thickness of the aluminum and magnesium fluoride layers. FIG. 12 depicts a graph of transmittance for the neutral density filter coating 124 having an optical density of 1.0. As can be seen in FIG. 12, the transmittance is about 10% across the UVC band. Further, FIG. 13 depicts a graph of reflectance for the neutral density filter coating 124 having an optical density of 1.0. The reflectance is about 80% across the UVC band, and thus, in view of the 10% transmittance and the 80% reflectance, only about 10% of the UVC light is absorbed. Advantageously, the UVC light reflected from the coating 124 can be redirected from the curved reflector surface 120 through the exit aperture 110. In this way, the UVC light emitted from the line emitter 116 is efficiently used for disinfecting of a surface.

Figure 14:
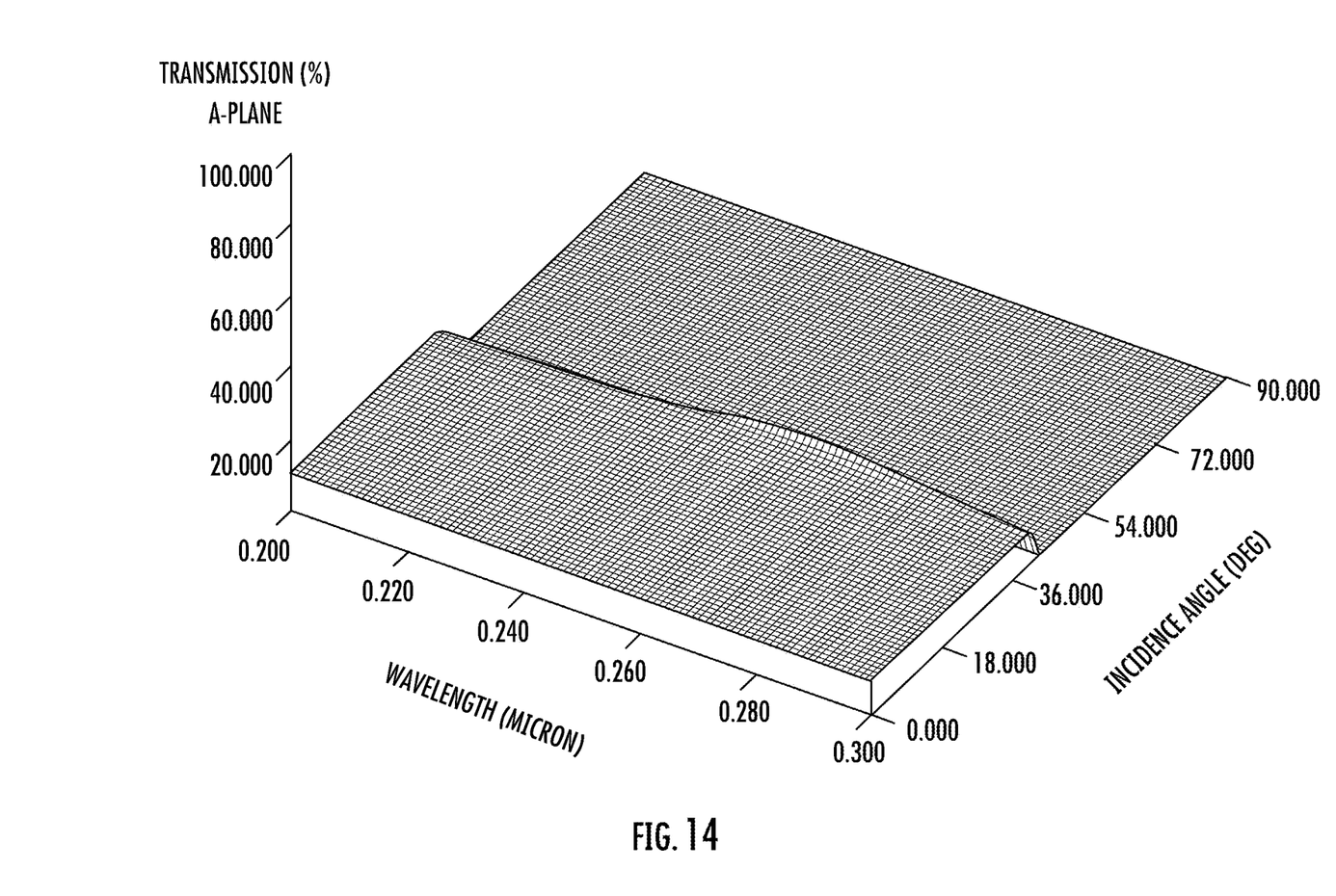

FIG. 14 further demonstrates transmittance of incident light in the UVC band as a function of incident angle from the curved reflector surface 120. As can be seen, the transmittance is about 10% over the UV band between 200 nm and 300 nm. The transmittance remains at about 10% until the incident angle reaches approximately 40°. Thereafter, the transmittance drops to 0% as a result of total internal reflection.

Figure 4:
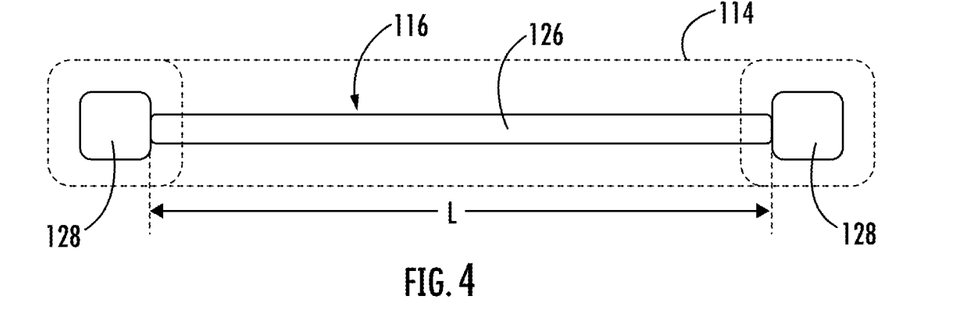
FIG. 4 depicts a light diffusing rod in a housing of the surface illuminator with two light sources, according to an exemplary embodiment.

Referring again to FIG. 3, the line emitter 116 can be any of a variety of suitable elements that emit UVC light in a substantially uniform manner along an emission length of the line emitter 116. In a particular embodiment, the line emitter 116 is a light diffusing rod 126. FIG. 4 schematically depicts the light diffusing rod 126 positioned within the housing 114. In embodiments, the light diffusing rod 126 has at least one end coupled to a UVC light source 128, such as a UVC light emitting diode (LED). Other UV light sources that can be coupled to the light diffusing rod 126 include lamps, lasers, diodes, and laser diodes. Further, in other embodiments, an optical element is used to couple the light diffusing rod 126 to the light source 128. In embodiments, the optical element may collect, collimate, focus, and/or otherwise process light supplied from a light source 128. For example, the optical element may be a solid glass element, a solid polymer or plastic element, a glass or polymer optical fiber, a lens, or other coupling element. In certain embodiments, each end of the light diffusing rod 126 is coupled to a UVC light source 128, e.g., at opposite ends of the housing 114.

The light-diffusing rod 126 has a maximum cross-sectional dimension and a length dimension. As shown in FIG. 4, the length dimension L is the dimension in the direction in which light propagates through the light diffusing rod 126, and the cross-sectional dimension may be the direction transverse to the direction of light propagation. The length of the light diffusing rod 126 may be at least 1 cm, or at least 5 cm, or at least 20 cm, or at least 50 cm, or at least 100 cm, or at least 500 cm. The length of the light diffusing rod 126 may be between 1 cm and 500 cm, or between 1 cm and 100 cm, or between 1 cm and 50 cm, or between 1 cm and 20 cm, or between 5 cm and 100 cm, or between 5 cm and 50 cm, or between 5 cm and 20 cm. In most applications, the length of the light diffusing rod 126 is no more than 1 m, although this limit is illustrative only. The specifics of a particular application and diffusive properties of the rod will inform each specific embodiment.

In embodiments in which the light diffusing rod 126 is cylindrical, the cross-section is circular, and the maximum cross-sectional dimension is a diameter of the circular cross-section. However, in other embodiments, the cross-section of the light diffusing rod defines a shape having one or more round or flat sides. For example, in embodiments, the shape of the cross-section is selected from circle, oval, square, rectangle, triangle, polygon, and shapes including a combination of round and flat sides (such as a semi-circle or semi-ellipse). In embodiments, the narrowest and/or flattest side would be directed towards the curved reflector surface 120 to approximate an idealized line source. As used herein, the maximum cross-sectional dimension refers to the longest straight-line distance that connects two points of the outline (e.g. circumference, perimeter) of the cross-section.

Figure 5:
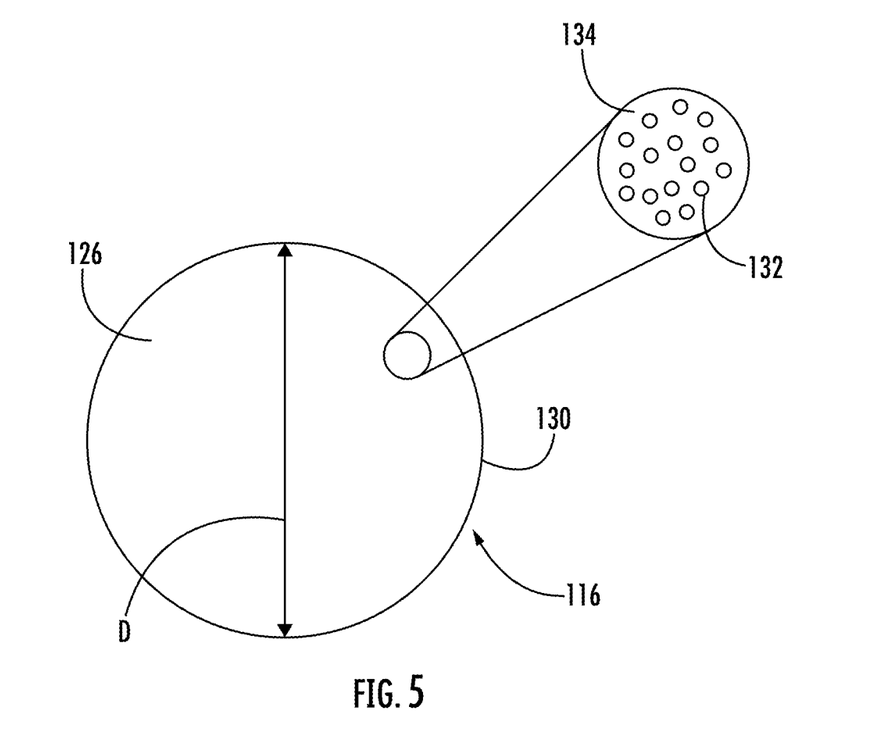
FIG. 5 depicts a cross-sectional view of a light diffusing rod, according to a first exemplary embodiment.

FIG. 5 depicts an example cross-section of a cylindrical light diffusing rod 126. In embodiments, the light diffusing rod 126 has a maximum cross-sectional dimension D of at least at least 0.1 mm, or at least 0.5 mm, or at least 1 mm, or at least 2 mm. In embodiments, the light diffusing rod 126 has a maximum cross-sectional dimension in the range of 0.1 mm to 20 mm, or between 0.1 mm and 15 mm, or between 0.1 mm and 10 mm, or between 0.1 mm and 5 mm, 0.5 mm to 20 mm, or between 0.5 mm and 15 mm, or between 0.5 mm and 10 mm, or between 0.5 mm and 5 mm, 1 mm to 20 mm, or between 1 mm and 15 mm, or between 1 mm and 10 mm, or between 1 mm and 5 mm, or between 2 mm and 20 mm, or between 2 mm and 10 mm, or between 2 mm and 15 mm, or between 2 mm and 5 mm.

The light diffusing rod 126 is configured to scatter light propagating along the length of the light diffusing rod 126 through an outer surface 130 of the light diffusing rod 126. In order to propagate and scatter light along its length, the light diffusing rod 126 is formed from a material with low UV absorption and, in particular, a material substantially free from UV absorbing defects or elements. For example, in embodiments, the material of the light diffusing rod 126 absorbs no more than 10% of light having a peak wavelength in the range of 100 nm to 400 nm over its length. Further, in embodiments, the material of the light diffusing rod 126 is free of defects that absorb 10% or more of ultraviolet light having a peak wavelength in the range of 100 nm to 400 nm. In embodiments, the light diffusing rod 126 is formed from high purity fused silica.

In order to scatter light propagating along the length of the light diffusing rod 126, the light-diffusing rod 126 comprises internal voids. Light passing longitudinally along the length of the light diffusing rod 126 is scattered by the internal voids in a direction transverse to the longitudinal axis of the light diffusing rod 126.

In embodiments, the internal voids have a cross-section with a dimension in the range from a few hundred nanometers to several microns. In exemplary embodiments, the cross-sectional dimension of the internal voids is from 100 nm to 20 µm, or from 500 nm to 10 µm, or from 500 nm to 5 µm. Further, the internal voids have a length in the range from a few microns to a few millimeters. In exemplary embodiments, the length of the internal voids is from 1 µm to 5 mm, or from 3 µm to 2 mm, or from 5 µm to 1 mm. In embodiments, the internal voids within the light diffusing rod 126 include a distribution of cross-sectional dimensions and lengths. Further, in embodiments, the internal voids may be configured in a random or non-periodic arrangement.

In embodiments, the internal voids occupy a fill fraction of 0.5% to 20% of the light diffusing rod 126, or 1% to 15% of the light diffusing rod 126, or 2% to 10% of the light diffusing rod 126. As used herein, fill fraction refers to the fraction of the cross-sectional area occupied by the internal voids. To a good approximation, the fill fraction corresponds to the volume fraction of internal voids. Thus, in embodiments, the volume fraction of voids within the light diffusing rod 126 is from 0.5% to 20%, or 1% to 15%, or 2% to 10%.

Figure 6:
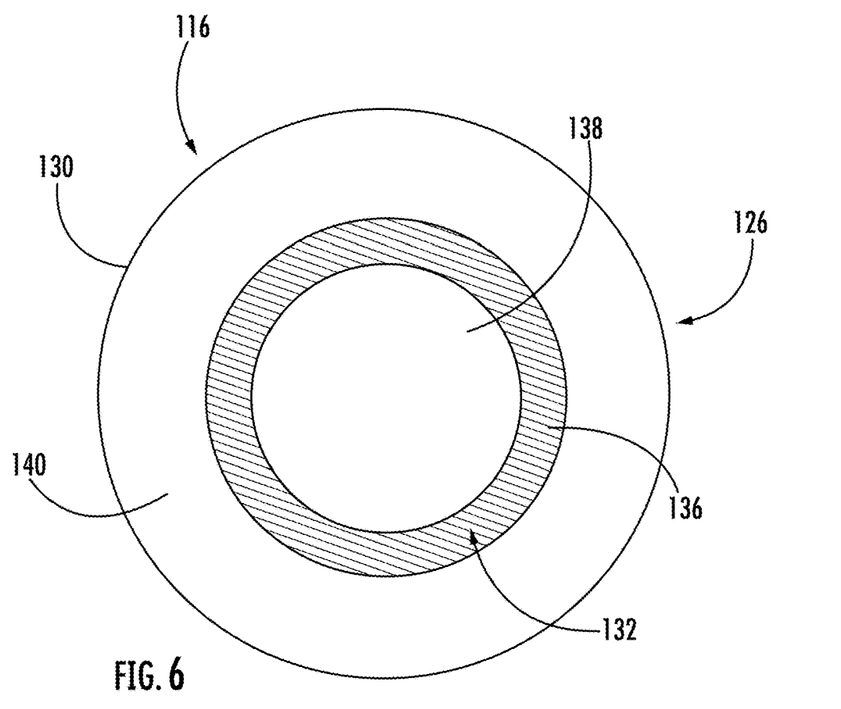
FIG. 6 depicts a cross-sectional view of a light diffusing rod having an annular structured region, according to a second exemplary embodiment.

In certain embodiments, the internal voids are distributed throughout the cross-section of the light diffusing rod 126, and in other embodiments, the internal voids are localized within one or more discrete regions of the light diffusing rod 126. FIGS. 5 and 6 illustrate examples of two spatial distributions of internal voids within the light diffusing rod 126.

FIG. 5 depicts a cross-section of a light-diffusing rod 126 in which the internal voids 132 are distributed throughout the cross-section. In the detail view of FIG. 5, it can be seen that the internal voids 132 are distributed within the low UV absorbing material 134 of the light diffusing rod 126. In FIG. 5, the internal voids 132 are shown as having substantially uniform cross-sectional size and shape, but in practice, a distribution of sizes and shapes for the internal voids 132 will be present.

FIG. 6 depicts a cross-section of a light diffusing rod 126 in which the internal voids are localized in an annular structured region 136. In this way, the cross-section of the light diffusing rod 126 includes an inner region 138 substantially free of any internal voids separated from an outer region 140 substantially free of any internal voids by the annular structured region 136 containing internal voids 132. In embodiments, the inner region 138 and the outer region 140 comprise solid high purity fused silica or another low UV absorbing material. In embodiments, the annular structured region 136 comprises a width that is in the range from 5% to 90% of the cross-sectional dimension of the light-diffusing rod 126, or from 10% to 90% of the cross-sectional dimension of the light-diffusing rod 126, or from 30% to 90% of the cross-sectional dimension of the light-diffusing rod 126.

In each of the embodiments of the light diffusing rod 126, including the exemplary embodiments depicted in FIGS. 5 and 6, the cross-sectional distribution of internal voids 132 may vary at different positions along the length of the light-diffusing rod 126. As noted, the length and cross-sectional attributes (e.g. shape and size) of the internal voids 132 may vary. The variations may also occur in the axial or length direction of the element. Since the length of the internal voids may not extend the full length of the element, particular internal voids may be present in some cross-sections and absent in other cross-sections.

In embodiments, the internal voids 132 are filled with a gas. Suitable gases include $SO_2$, noble gases, $CO_2$, $N_2$, $O_2$, air, or mixtures thereof.

The light-diffusing rod 126 may be configured to scatter light along all or some of its length by controlling the placement of the internal voids 132. Regions of the light diffusing rod 126 that include a high volume fraction of internal voids 132 may scatter more light than regions of the light diffusing rod 126 having a lower volume fraction of internal voids 132. In this way, the scattering intensity along the length of the light diffusing rod 126 can be made uniform by, e.g., increasing the volume fraction of internal voids 132 along the length of the light diffusing rod 126 as the distance from the light source 128 increases. If two light sources 128 are provided at opposing ends of the light diffusing rod 126, then, for example, the highest fill fraction of voids may be provided at or near the midpoint of the light diffusing rod 126.

The intensity of ultraviolet emission from the light-diffusing rod 126 relates to the efficiency at which the surface illuminator 100 provides the disinfecting action. In this regard, a higher scattering loss generally increases the intensity of emission of the light-diffusing rod 126. In embodiments, the scattering loss is at least 0.1 dB/m, or at least 1 dB/m, or at least 5 dB/m, or at least 100 dB/m.

As mentioned, the light diffusing rod 126 can be configured to provide uniform intensity along the length of the light-diffusing rod 126. Uniformity of intensity can be considered in terms of the maximum and minimum intensity of scatter light passing through the outer surface 130 of the light diffusing rod 126. In embodiments, a light diffusing rod 126 having a substantially uniform intensity has a minimum intensity of scattered light that is within 30%, in particular within 20%, and more particularly within 10% of the maximum intensity of scattered light in the ultraviolet band (i.e., 100 nm to 400 nm).

Information regarding the fabrication and the processing of the light diffusing rods 126 described herein may be found in U.S. Pat. Nos. 7,450,806 and 8,926,143, the disclosures of which are incorporated herein in their entirety by reference thereto.

Figure 7:
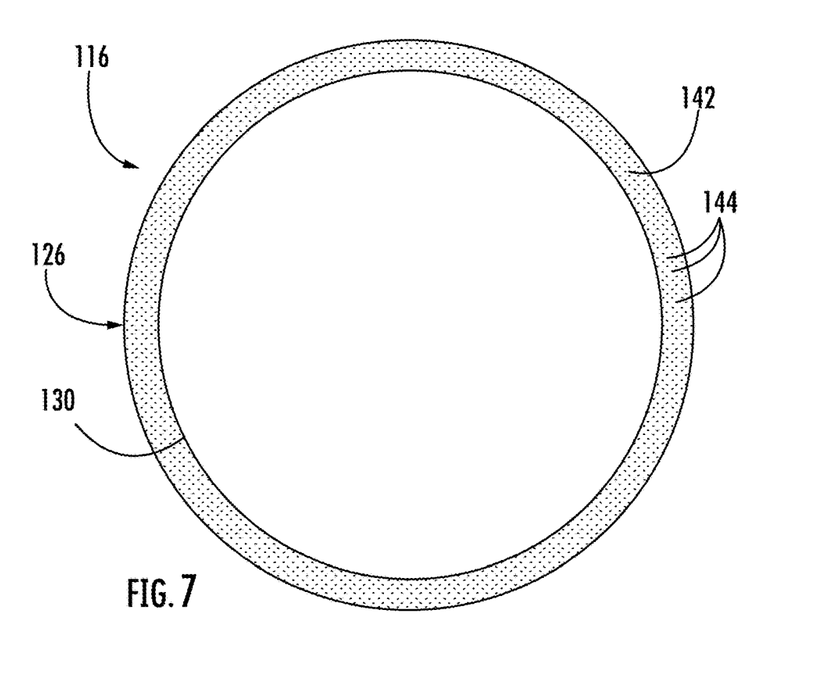
FIG. 7 depicts a cross-sectional view of a light diffusing rod having a surface coating, according to an exemplary embodiment.

In the embodiment shown in FIG. 7, the light-diffusing rod 126 includes a surface coating 142. In embodiments, the surface coating 142 is in direct contact with the outer surface 130 of the light-diffusing rod 126. In certain such embodiments, the light-diffusing rod 126 may lack a cladding typically associated with light diffusing optical fibers and instead have a cladding provided by ambient air. In embodiments, the surface coating 142 is a curable composition or a thin shrink tubing. Further, in embodiments, the surface coating 142 comprises a material having a high transmittance (e.g., 70% or more) of ultraviolet light having a peak wavelength in the range of 100 nm to 400 nm through the thickness of the surface coating 142. In particular embodiments, the surface coating 142 comprises a fluoropolymer or a cyclic olefin copolymer. More particular, the surface coating 142 comprises a material having a lower refractive index than the light diffusing rod 126. In embodiments, the thickness of the surface coating is 100 µm or less, more particularly 25 µm or less.

In embodiments, the surface coating 142 includes a scattering layer that may control or modify the angular distribution of light scattered by the internal voids 132, e.g., to enhance the distribution and/or the nature of the scattered light. For example, in such embodiments, surface coating 142 may include scattering material 144 that may make the angular distribution of light scattered by the internal voids more uniform.

In embodiments, the scattering material 144 comprises nano- or microparticles with an average diameter of from about 200 nm to about 10 µm. In exemplary embodiments, the average diameter of the scattering particles may be about 200 nm, or 300 nm, or 400 nm, or 500 nm, or 600 nm, or 700 nm, or 800 nm, or 900 nm, or 1 µm, or 2 µm, or 3 µm, or 4 µm, or 5 µm, or 6 µm, or 7 µm, or 8 µm, or 9 µm, or 10 µm. The concentration of the scattering material 144 may vary along the length of the element or may be constant and may be present in a weight percent sufficient to provide uniform scattering of light while limiting overall attenuation. The weight percentage of the scattering particles in the scattering layer may comprise about 1%, or 2%, or 3%, or 4%, or 5%, or 6%, or 7%, or 8%, or 9%, or 10%, or 11%, or 12%, or 13%, or 14%, or 15%, or 16%, or 17%, or 18%, or 19%, or 20%, or 25%, or 30%, or 35%, or 40%, or 45%, or 50%. The surface coating 142 may comprise small particles or colloids of a scattering material that may include a metal oxide or other high refractive index material, such as $TiO_2$, $Al_2O_3$, ZnO, $SiO_2$, or Zr. The scattering material may also comprise micro- or nanosized particles or voids of low refractive index, such as gas bubbles. The width of the scattering layer may be greater than about 1 µm, or 2 µm, or 3 µm, or 4 µm, or 5 µm, or 6 µm, or 7 µm, or 8 µm, or 9 µm, or 10 µm, or 20 µm, or 30 µm, or 40 µm, or 50 µm, or 60 µm, or 70 µm, or 80 µm, or 90 µm, or 100 µm.

In a particular embodiment, the scattering material 144 comprises $TiO_2$-based particles, such as a white ink, which provides for substantially angle-independent distribution of light scattered from the internal voids of the light-diffusing rod 126.

Further, in embodiments, the scattering material 144 occupies a sublayer within the surface coating 142. For example, the scattering material 144 may be localized to a layer having a thickness of about 1 µm to about 5 µm.

In embodiments, the surface coating 142 may be a protective polymer jacket or tube. The polymer jacket may include a scattering material or component, either internally as a filler or applied to the external surface of the jacket (e.g. a white diffusing paint), to make the angular distribution of light intensity from the element more uniform.

The polymer jacket may be incorporated as a surrounding layer with a scattering layer. A scattering layer may surround the light-diffusive element and the polymer jacket may surround the scattering layer. The scattering layer may be in direct contact with the polymer jacket and/or in direct contact with the outer surface 130 of the light-diffusing rod 126.

In general and with reference back to FIG. 3, a light diffusing rod 126 is configured to emit light radially or circumferentially through the entire perimeter of the outer surface 130. However, the ultraviolet light for the surface illuminator 100 is designed to shine through the exit aperture 110, and thus, it is desirable that ultraviolet light emitted from the light diffusing rod 126 is efficiently directed at the curved reflector surface 120 for maximum output through the exit aperture 110. For this reason, in embodiments, the light diffusing rod 126 is configured to emit light through less than the entire perimeter of the light diffusing rod 126, in particular through 50% or less of the perimeter. Accordingly, in embodiments, the light diffusing rod 126 or other non-directional line emitter 116 is disposed in a reflective jacket 146 as shown in FIGS. 8 and 9.

Figure 8:
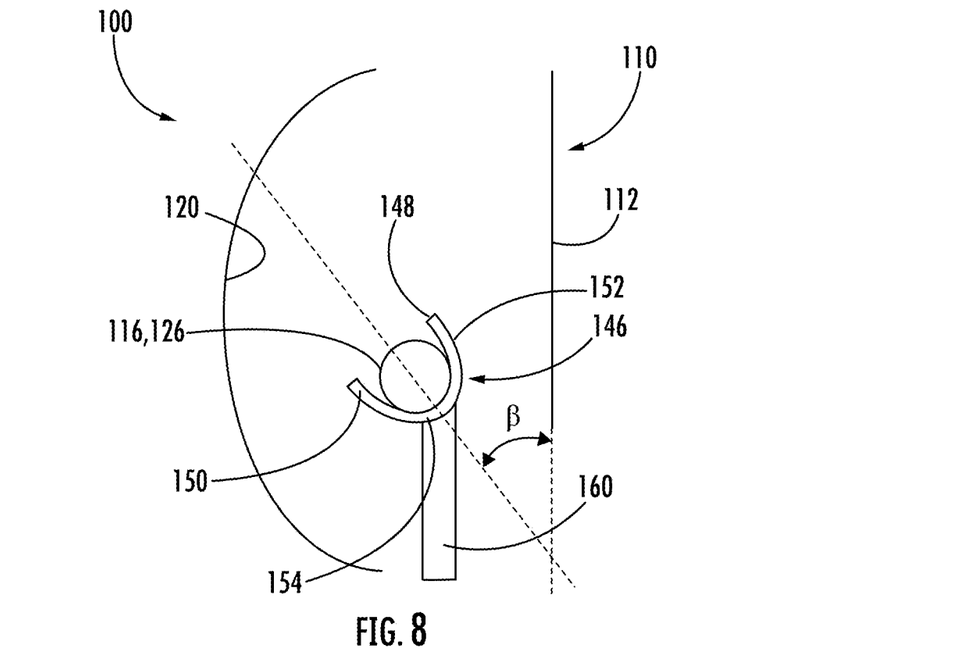
FIG. 8 depicts a schematic representation of a surface illuminator having a line emitter with a reflecting jacket trough, according to a first exemplary embodiment.

Referring first to FIG. 8, the reflective jacket 146 is depicted in the form of a trough 148. In embodiments, the trough 148 comprises a plastic or metal, such as aluminum. Further, in embodiments, the trough 148 may comprise a highly reflective diffuser material, such as phase separated glass tube. As can be seen, the trough 148 includes a first sidewall 150 and a second sidewall 152 connected by a curved wall 154, thereby defining a U-shape. The trough 148 includes a reflective inner surface designed to direct light emitted by the light diffusing rod 126 or line emitter 116 through the open end between sidewalls 150, 152. In embodiments, the open end between the sidewalls 150, 152 has a width that is approximately equal to the maximum cross-sectional dimension of the line emitter 116 or light diffusing rod 126. In other embodiments in which the line emitter or light diffusing rod 126 is not cylindrical, the width between the sidewalls 150, 152 may be approximately equal to the smallest side length of the polygonal cross-section or a minor axis of a curved polygonal cross-section.

Figure 9:
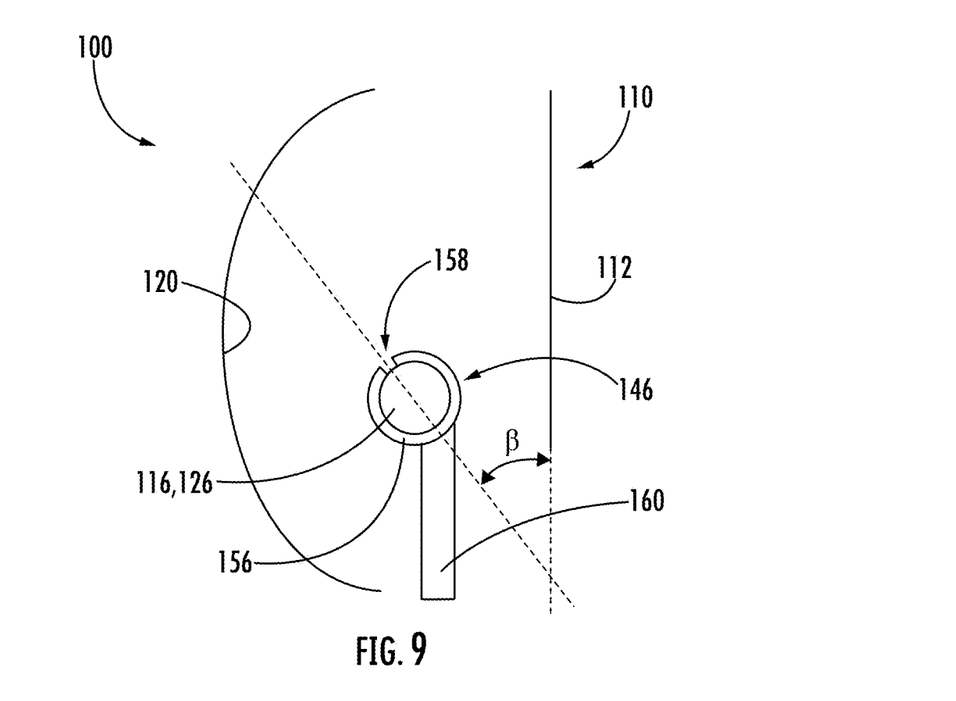
FIG. 9 depicts a schematic representation of a surface illuminator having a line emitter with a reflective jacket coating, according to a second exemplary embodiment.

Referring now to FIG. 9, the reflective jacket 146 is depicted in the form of a coating 156 having a gap 158 through which light is emitted. In embodiments, the coating 156 is in the form of a deposited reflective material (such as aluminum). In such embodiments, a polymer shrink tube 142 may be applied outside the reflective coating to provide additional mechanical support for the line emitter 116 or light diffusing rod 126. In embodiments, the width of the gap 158 is determined by power transmission and the focal length of the curved reflector surface 120. In particular, the gap 148 is preferably as small as practicable to approximate an idealized line source. In an example embodiment, the gap 148 was 1 mm.

With reference to both FIGS. 8 and 9, the reflective jacket 146 is configured to direct light at the curved reflector surface 120. In this regard, embodiments of the surface illuminator 100 arrange the open end or gap 158 of the reflective jacket 146 at a particular angle β relative to the second plane 112 of the exit aperture 110. In embodiments, the angle β is up to 30°. Still further, the reflective jacket 146 also allows for support elements 160 to be positioned along the length of the line emitter 116 or light diffusing rod 126 to provide further mechanical support without obscuring the ultraviolet light being emitted. In embodiments, the line emitter 116 or light diffusing rod 126 is supported by one or more support elements 160 along the length thereof.

Having described the structure the surface illuminator 100, the illumination properties will be described. The curved reflector surface 120 of the surface illuminator directs light out of the exit aperture 110. While the line emitter 116 is configured to emit a single continuous and substantially uniform line of ultraviolet light in order to make the most economical use of the ultraviolet light, the ultraviolet light leaving the exit aperture 110 will disperse over the surface to be illuminated. In general, regions nearer to the surface illuminator 100 will experience a greater intensity of ultraviolet light than regions farther away from the surface illuminator 100. In this regard, it is desirable that the lowest intensity of illumination is still effective for disinfecting the surface and that the highest intensity of illumination will not damage the surface (e.g., the display and/or touch functionality of the surface).

Figure 10:
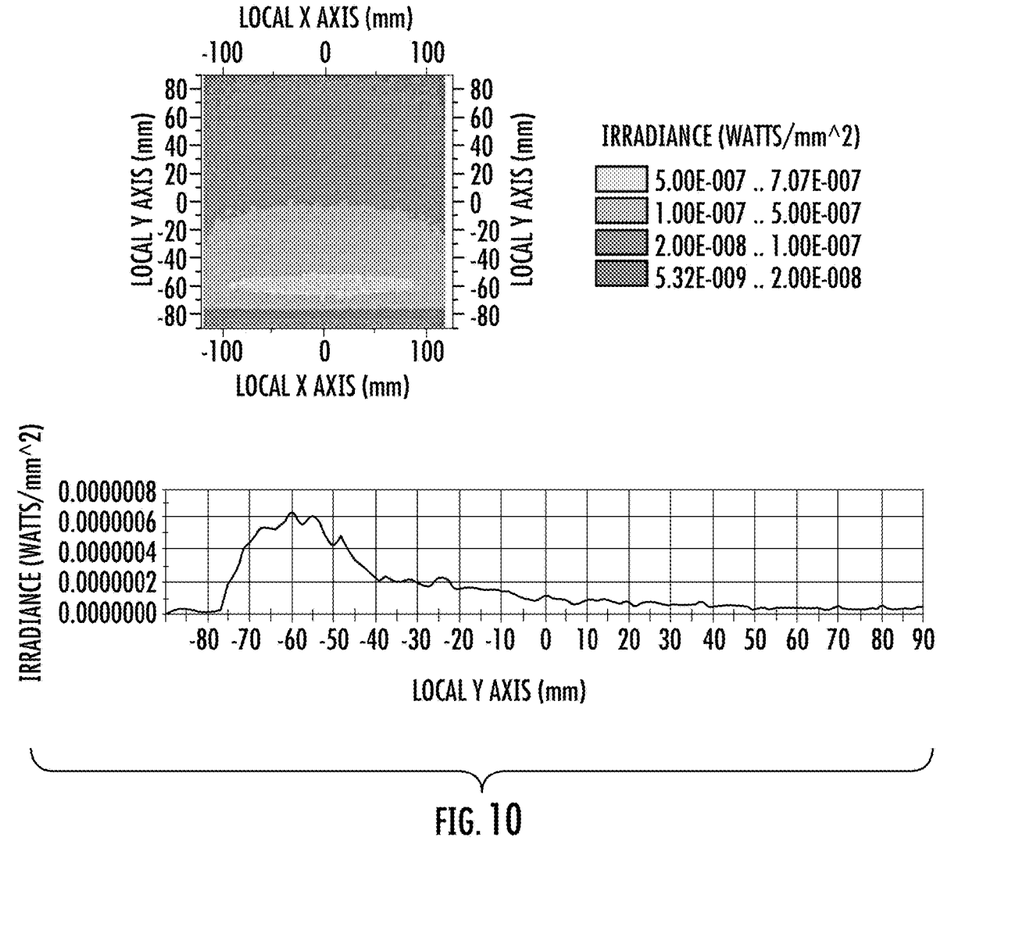
FIGS. 10 and 11 depict plots of irradiance for two surface illuminators having different angles at which light is incident on the curved reflector surface, according to exemplary embodiments.

FIG. 10 depicts a plot of the irradiance (W/mm$^2$) for a surface illuminated by an embodiment of the surface illuminator 100. The surface illuminator 100 modeled to produce the graph considered a line emitter positioned 1 mm from an edge of the surface and 4 mm above the surface. The surface was angled 1° relative to horizontal (i.e., the angle α between the first plane 108 of the surface 104 and the second plane 112 of the exit aperture 110 as shown in FIG. 2 was 89°). A third of the window 122 of the exit aperture 110 had a neutral density filter coating 124 with an optical density of 2, and the opening or gap of the reflective jacket 146 around the line emitter 116 was angled at 20° (i.e., angle β was 20° relative to the second plane 112 of the exit aperture 110).

As shown in FIG. 10, the intensity is greatest between −100 mm and 100 mm on the x-axis between about −50 mm and −70 mm on the y-axis. In the graph beneath the plot of FIG. 10, the irradiance along the y-axis at x=0 mm is shown. Again, the peak irradiance is shown to be between about −50 mm and −70 mm.

Figure 11:
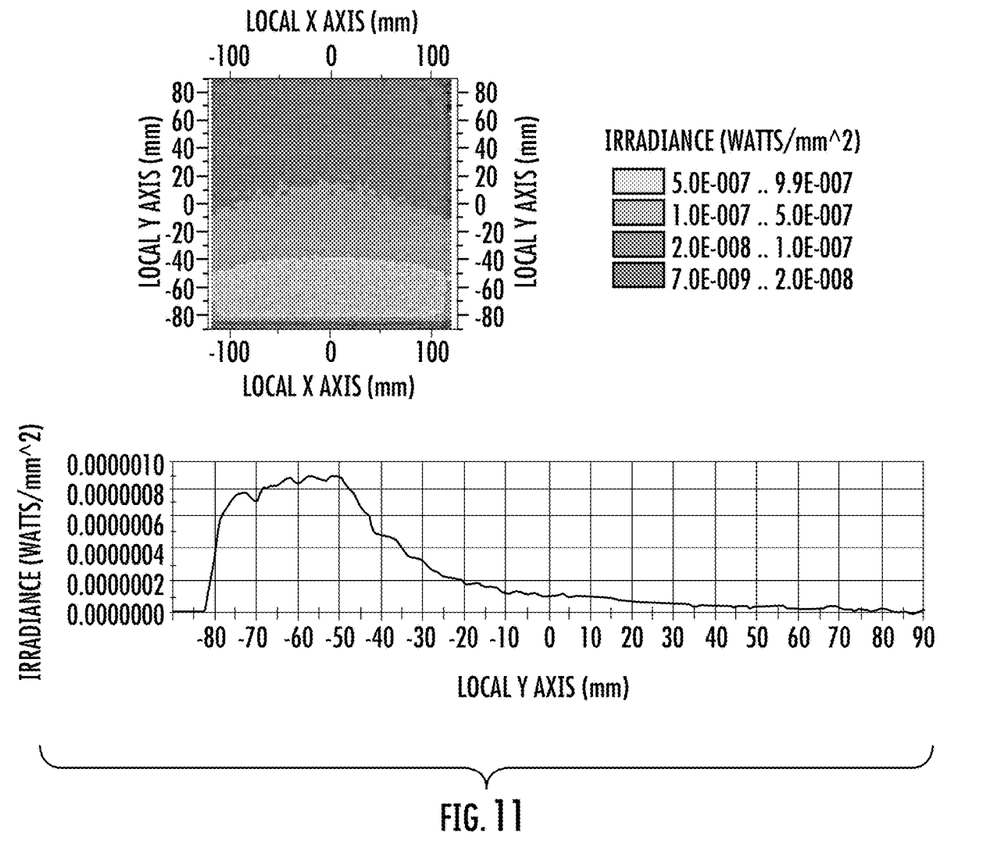

FIG. 11 depicts a plot of irradiance similar to what is shown in FIG. 10 with the exception that the surface illuminator 100 was modeled with angle β at 10°, instead of 20°. As can be seen the region of peak intensity is increased in magnitude and in length and width. In particular, the width of the peak region is expanded beyond −100 mm and 100 mm along the x-axis, and the length of the peak region is expanded between about −75 mm and −45 mm.

Thus, FIGS. 10 and 11 demonstrate that the angle β at which the line emitter 116 is arranged with respect to the curved reflector surface 120 can increase or decrease the irradiance as needed to meet the requirements of disinfecting for the surface as well as to avoid damage to the surface.

Figure 15:
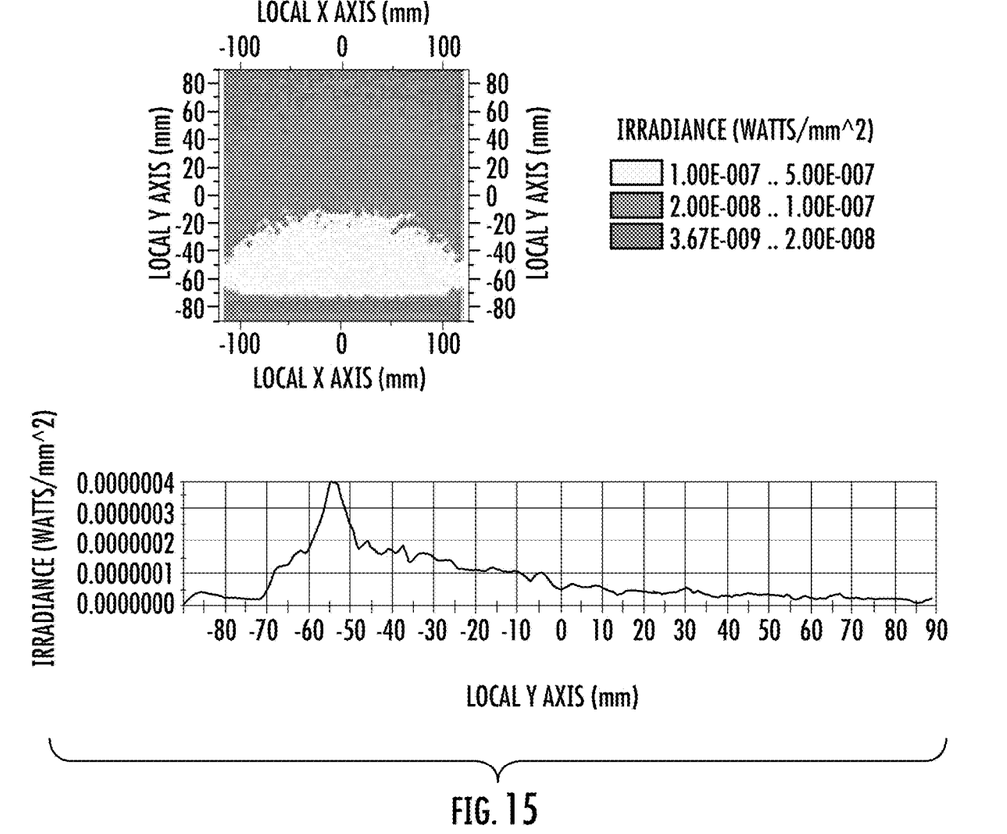
FIGS. 15 and 16 depict plots of irradiance for two surface illuminators having different optical densities of the neutral density filter coating.
Figure 16:
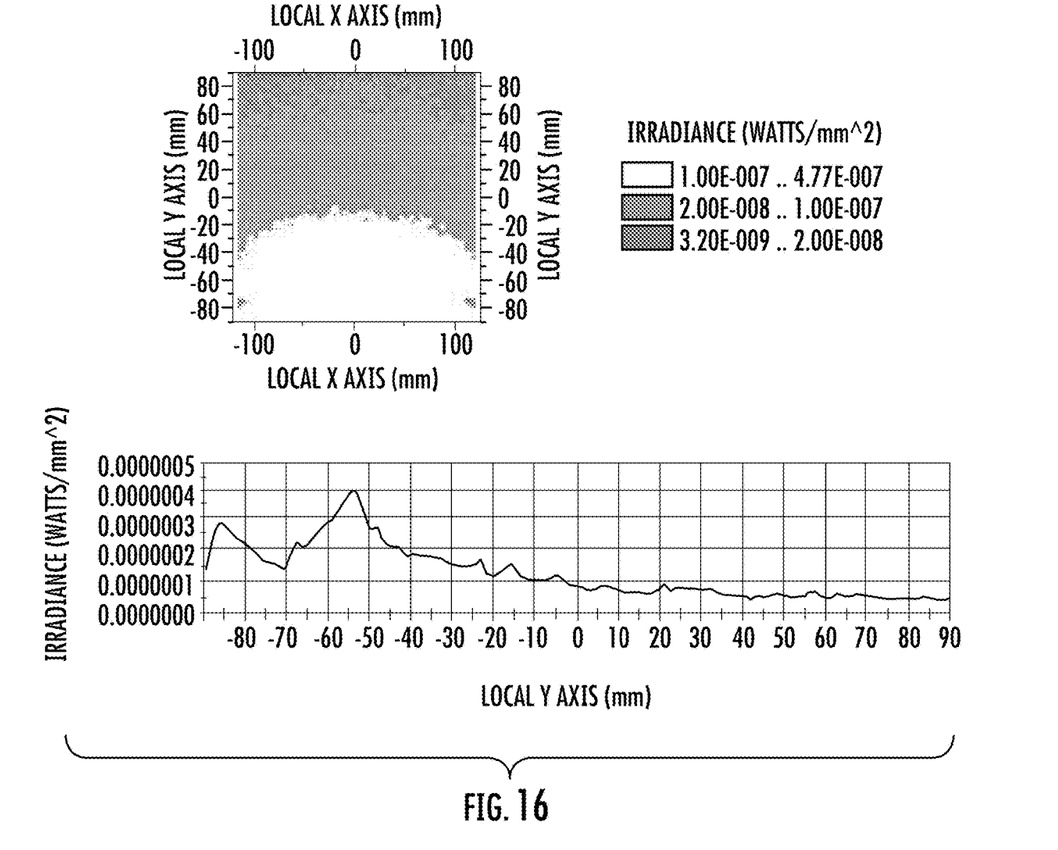

FIGS. 15 and 16 demonstrate the effect of the optical density of the neutral density filter coating 124. The surface illuminator 100 considered in FIGS. 15 and 16 was modeled as described above in relation to FIGS. 10 and 11 except that the angle β is set at 25° for both FIGS. 15 and 16. In the plot of FIG. 15, the model considers a neutral density filter coating 124 with an optical density of 2.0, and in the plot of FIG. 16, the model considers a neutral density filter coating 124 with an optical density of 1.0.

In FIG. 15, the peak irradiance extends the entire width of the surface, and the peak has a length between about −70 mm and about −10 mm on the y-axis; although, the largest peak is primarily between about −60 mm and about −50 mm. However, the irradiance leading up to the peak (−80 mm to −70 mm) is relatively low compared to the end of the peak (e.g., from 40 mm to 90 mm).

In FIG. 16, the irradiance plot and graph demonstrate dual peaks. One peak shown in FIG. 16 is located in substantially the same position as the peak of FIG. 15 (i.e., between −60 mm and −50 mm), and the peak has approximately the same magnitude. The other peak shown in FIG. 16 is between about −100 mm and −80 mm on the y-axis. Overall, the dual peaks of irradiance expand the coverage of ultraviolet light at the end of the surface where the surface illuminator is positioned. Thus, FIGS. 15 and 16 demonstrate that the level of optical density of a neutral density filter can be used to manipulate the irradiance of the surface illuminator.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that any particular order be inferred. In addition, as used herein, the article "a" is intended to include one or more than one component or element, and is not intended to be construed as meaning only one.

It will be apparent to those skilled in the art that various modifications and variations can be made without departing from the spirit or scope of the disclosed embodiments. Since modifications, combinations, sub-combinations and variations of the disclosed embodiments incorporating the spirit and substance of the embodiments may occur to persons skilled in the art, the disclosed embodiments should be construed to include everything within the scope of the appended claims and their equivalents.

What is claimed is:

1. An illuminator for disinfecting a surface defining a first plane, comprising:
   a line emitter configured to emit light in a continuous line, the line emitter comprising a light diffusing rod structured to scatter light along its length, the light diffusing rod comprising at least one of: (i) a scattering layer, (ii) scattering particles, or (iii) voids; and
   a reflector surface optically coupled to the line emitter;
   wherein the light diffusing rod is optically coupled to at least one light source and has a maximum cross-sectional dimension D between 0.5 mm to 20 mm;
   wherein the line emitter is structured to provide the light to at least a portion of the surface, and the light has a peak wavelength in a range of 100 nm to 400 nm;
   wherein the reflector surface is configured to redirect the light from the line emitter towards the surface; and
   wherein the light diffusing rod is at least partially enclosed in a jacket and wherein the jacket comprises a reflective internal surface configured to direct light at the reflector surface.

2. The illuminator of claim 1, further comprising an exit aperture defining a second plane transverse to the first plane; wherein the line emitter is positioned between the reflector surface and the exit aperture.

3. The illuminator of claim 1, wherein said reflector surface is a curved reflector surface.

4. The illuminator for disinfecting a surface defining a first plane of claim 1, wherein the emitter comprises a light emitting surface providing uniform illumination intensity over its length, such that the emitter has a minimum intensity of scattered light that is within 30% of the maximum intensity of scattered light within said band.

5. The illuminator for disinfecting a surface defining a first plane of claim 1, wherein
   the emitter comprises a light emitting surface and is configured to emit light in a continuous line along at least a portion of the surface has the maximum cross-sectional dimension D of less than 5 mm.

6. The illuminator for disinfecting a surface defining a first plane of claim 1, wherein the line emitter comprises a comprises a waveguide with glass core and a light emitting surface.

7. The illuminator of claim 1 wherein the light diffusing rod comprises a material that absorbs less than 10% of light in the range of 100 nm to 400 nm along the continuous line.

8. The illuminator of claim 7, wherein the material is free of defects that absorb more than 10% of light in the range of 100 nm to 400 nm along the continuous line.

9. The illuminator of claim 7, wherein the material comprises fused silica.

10. The illuminator of any of claim 1, wherein the light diffusing rod comprises a perimeter and wherein the light diffusing rod is configured to emit light through less than the entire perimeter.

11. The illuminator of claim 10, wherein the light diffusing rod is configured to emit light through less than 50% of the perimeter.

12. The illuminator of claim 1, wherein the jacket is a trough comprising two side walls joined by a third wall at a first end and wherein the two sidewalls define an opening at a second end opposite to the first end.

13. The illuminator of claim 1, wherein the light diffusing rod comprises an outer surface, wherein the jacket is a reflective coating extending around the outer surface of the light diffusing rod, and wherein the reflective coating defines a gap along a length of the light diffusing rod through which the outer surface is exposed.

14. The illuminator of claim 1, further comprising a coating surrounding an outer surface of the light diffusing rod, the coating comprising a plurality of scattering structures.

15. The illuminator of claim 1, further comprising a thin shrink tubing surrounding an outer surface of the light diffusing rod.

16. The illuminator of claim 15, wherein the thin shrink tubing comprises a plurality of scattering structures.

17. The illuminator of claim 14, wherein the coating or the thin shrink tubing comprises a polymer that absorbs less than 15% of light in the range of 100 nm to 400 nm through a thickness of the coating or of the thin shrink tubing.

18. The illuminator of claim 17, wherein the polymer is a fluorinated polymer or cyclic olefin copolymer.

19. The illuminator of claim 1, wherein the light diffusing rod comprises a core of a material that absorbs less than 1% of light in the range of 100 nm to 400 nm along the continuous line.

20. The illuminator of claim 19, wherein ambient air serves as a cladding for the core.

21. The illuminator of claim 1, wherein the light diffusing rod comprises a core and a cladding surrounding the core and wherein the core, the cladding, or both the core and the cladding comprise scattering material.

22. The illuminator of claim 21, wherein the scattering material is free from defects that absorb light in the range of 100 nm to 400 nm.

23. The illuminator of claim 1, wherein the light diffusing rod comprises a circular cross-section or a non-circular cross-section.

24. The illuminator of claim 23, wherein the non-circular cross-section comprises an elliptical cross-section, a rectangular cross-section, a triangular cross-section, a semi-circular cross-section, or a semi-elliptical cross-section.

25. The illuminator of claim 1, wherein the light diffusing rod comprises internal voids.

26. The illuminator of claim 2, further comprising a window disposed in the exit aperture, wherein the window comprises a material that transmits at least 70% of light in the range of 100 nm to 400 nm through a thickness of the window.

27. The illuminator of claim 1, wherein the reflector surface is curved and a cylindrical.

28. The illuminator of any of the preceding claims of claim 2, wherein the first plane and the second plane form an angle of 70° to 90°.

29. An illuminator for disinfecting a surface defining a first plane, comprising:
   a line emitter configured to emit light in a continuous line, the line emitter comprising a light diffusing rod structured to scatter light along its length, the light diffusing rod comprising at least one of: (i) a scattering layer, (ii) scattering particles, or (iii) voids;
   a curved reflector surface optically coupled to the line emitter; and
   an exit aperture defining a second plane transverse to the first plane;
   wherein the line emitter is positioned between the reflector surface and the exit aperture;
   wherein the light diffusing rod is optically coupled to at least one light source and has a maximum cross-sectional dimension D between 0.5 mm and 20 mm;
   wherein the line emitter is structured to provide the light to at least a portion of the surface, and the light has a peak wavelength in a range of 100 nm to 400 nm;
   wherein the curved reflector surface is configured to redirect the light from the line emitter towards the surface;
   wherein the light diffusing rod is at least partially enclosed in a jacket and wherein the jacket comprises a reflective internal surface;
   wherein the jacket is a trough comprising two side walls joined by a third wall at a first end and wherein the two sidewalls define an opening at a second end opposite to the first end; and
   wherein the opening is oriented to direct light across the exit aperture after reflecting off the curved reflector surface.

30. The illuminator of claim 29, wherein the opening is oriented toward the curved reflective surface at an angle of 0° to 30° relative to the second plane defined by the exit aperture.

31. An illuminator for disinfecting a surface defining a first plane, comprising:
   a line emitter configured to emit light in a continuous line, the line emitter comprising a light diffusing rod structured to scatter light along its length, the light diffusing rod comprising at least one of: (i) a scattering layer, (ii) scattering particles, or (iii) voids;
   a reflector surface optically coupled to the line emitter;
   an exit aperture defining a second plane transverse to the first plane; and
   a window disposed in the exit aperture;
   wherein the line emitter is positioned between the reflector surface and the exit aperture;
   wherein the window comprises a material that transmits at least 70% of light in the range of 100 nm to 400 nm through a thickness of the window;
   wherein the light diffusing rod is optically coupled to at least one light source and has a maximum cross-sectional dimension D between 0.5 mm to 20 mm;

wherein the line emitter is structured to provide the light to at least a portion of the surface, and the light has a peak wavelength in a range of 100 nm to 400 nm;

wherein the reflector surface is configured to redirect the light from the line emitter towards the surface; and wherein the illuminator further comprises a neutral density filter disposed over a portion of the window.

32. The illuminator of claim 31, wherein the neutral density filter covers 50% or less of the window.

33. A surface illuminator configured to disinfect a surface having a first surface area, the surface illuminator comprising:

a line emitter optically coupled to at least one light source, said line emitter comprising a light diffusing rod structured to scatter light along its length and the said line emitter being configured to emit the scattered light in a continuous line along at least a portion of a surface of the light diffusing rod, the light having a peak wavelength in a range of 100 nm to 400 nm, wherein the light diffusing rod comprises a material comprising at least one of: (i) a scattering layer; (ii) scattering particles; or (iii) voids;

a curved reflector surface; and an exit aperture arranged transverse to a first plane defined by the surface;

wherein the curved reflector surface is configured to redirect the light from the line emitter through the exit aperture over at least 90% of the first surface area; and wherein the light diffusing rod is at least partially enclosed in a jacket and wherein the jacket comprises a reflective internal surface configured to direct light at the curved reflector surface.

34. A method for decontaminating a surface having a first surface area, the method comprising:

emitting light having a wavelength of 100 nm to 400 nm from a line emitter, the line emitter comprising a light diffusing rod structured to scatter light along its length and the line emitter being configured to emit the scattered light in a continuous line along at least a portion of a surface of the light diffusing rod, wherein the light diffusing rod comprises a material comprising at least one of: (i) a scattering layer; (ii) scattering particles; or (iii) voids;

directing scattered light toward a curved reflector surface using a reflective internal surface of a jacket that at least partially encloses the light diffusing rod; and reflecting the light from the curved reflector surface through an exit aperture and onto the surface, wherein the light irradiates at least 90% of the first surface area at a power density sufficient to disinfect the first surface area.

* * * * *

UNITED STATES PATENT AND TRADEMARK OFFICE
CERTIFICATE OF CORRECTION

PATENT NO. : 12,222,528 B2
APPLICATION NO. : 17/688142
DATED : February 11, 2025
INVENTOR(S) : Baarman et al.

It is certified that error appears in the above-identified patent and that said Letters Patent is hereby corrected as shown below:

In the Claims

Line 9 (Claim 28) delete "any of the preceding claims"

Signed and Sealed this
Twelfth Day of August, 2025

Coke Morgan Stewart
*Acting Director of the United States Patent and Trademark Office*